United States Patent
Nabutovsky et al.

(10) Patent No.: US 9,861,823 B2
(45) Date of Patent: Jan. 9, 2018

(54) CARDIAC RESYNCHRONIZATION SYSTEM AND METHOD

(71) Applicant: Pacesetter, Inc., Sunnyvale, CA (US)

(72) Inventors: Yelena Nabutovsky, Mountain View, CA (US); Hoda Razavi, San Jose, CA (US)

(73) Assignee: Pacesetter, Inc., Sunnyvale, CA (US)

( * ) Notice: Subject to any disclaimer, the term of this patent is extended or adjusted under 35 U.S.C. 154(b) by 237 days.

(21) Appl. No.: 14/703,757

(22) Filed: May 4, 2015

(65) Prior Publication Data

US 2015/0313495 A1 Nov. 5, 2015

Related U.S. Application Data

(60) Provisional application No. 61/988,771, filed on May 5, 2014.

(51) Int. Cl.
| | |
|---|---|
| *A61N 1/36* | (2006.01) |
| *A61N 1/368* | (2006.01) |
| *A61B 5/0452* | (2006.01) |
| *A61B 5/02* | (2006.01) |
| *A61N 1/365* | (2006.01) |
| *A61B 5/042* | (2006.01) |
| *A61N 1/362* | (2006.01) |

(Continued)

(52) U.S. Cl.
CPC .............. *A61N 1/3684* (2013.01); *A61B 5/02* (2013.01); *A61B 5/042* (2013.01); *A61B 5/0422* (2013.01); *A61B 5/0452* (2013.01); *A61B 5/061* (2013.01); *A61N 1/3627* (2013.01); *A61N 1/3682* (2013.01); *A61N 1/36514* (2013.01); *A61N 1/36592* (2013.01); *A61B 5/4836* (2013.01)

(58) Field of Classification Search
CPC ....... A61B 5/02; A61B 5/0422; A61B 5/0452; A61N 1/36592
See application file for complete search history.

(56) References Cited

U.S. PATENT DOCUMENTS

| | | | |
|---|---|---|---|
| 5,391,199 | A | 2/1995 | Ben-Haim |
| 5,713,367 | A | 2/1998 | Arnold et al. |
| 6,233,476 | B1 | 5/2001 | Strommer et al. |

(Continued)

FOREIGN PATENT DOCUMENTS

| | | |
|---|---|---|
| EP | 1 070 480 A2 | 1/2001 |
| EP | 1 508 300 A1 | 2/2005 |

(Continued)

OTHER PUBLICATIONS

Notice of Allowance dated Jun. 22, 2015; Related U.S. Appl. No. 14/328,523.

(Continued)

*Primary Examiner* — Amanda Patton
(74) *Attorney, Agent, or Firm* — Theresa A. Raymer

(57) ABSTRACT

Embodiments of the present disclosure provide a method of determining an inter-chamber delay within a heart of an individual that may include determining a position of a first sensor in a first chamber of the heart, determining a position of a second sensor in a second chamber of the heart, automatically computing a distance between the first and second sensors, and automatically determining the inter-chamber delay based on the automatically computing operation.

20 Claims, 3 Drawing Sheets

(51) Int. Cl.
*A61B 5/06* (2006.01)
*A61B 5/00* (2006.01)

(56) References Cited

U.S. PATENT DOCUMENTS

| | | | |
|---|---|---|---|
| 6,301,496 | B1 | 10/2001 | Reisfeld |
| 6,609,027 | B2 | 8/2003 | Kroll et al. |
| 6,633,686 | B1 | 10/2003 | Bakircioglu et al. |
| 6,728,562 | B1 | 4/2004 | Budd et al. |
| 6,751,492 | B2 | 6/2004 | Ben-Haim |
| 6,978,168 | B2 | 12/2005 | Beatty et al. |
| 7,197,354 | B2 | 3/2007 | Sobe |
| 7,263,397 | B2 | 8/2007 | Hauck et al. |
| 7,276,064 | B2 | 10/2007 | Paul et al. |
| 7,338,486 | B2 | 3/2008 | Sliwa et al. |
| 7,386,339 | B2 | 6/2008 | Strommer et al. |
| 7,505,809 | B2 | 3/2009 | Strommer et al. |
| 7,697,973 | B2 | 4/2010 | Stemmer et al. |
| 7,881,769 | B2 | 2/2011 | Sobe |
| 8,016,764 | B1 | 9/2011 | Shelchuk |
| 8,195,292 | B2 * | 6/2012 | Rosenberg ........... A61B 5/0422 600/374 |
| 8,849,381 | B2 | 9/2014 | Mason et al. |
| 9,162,067 | B1 | 10/2015 | Farazi et al. |
| 2003/0093067 | A1 | 5/2003 | Panescu |
| 2003/0233039 | A1 | 12/2003 | Shao et al. |
| 2005/0154282 | A1 | 7/2005 | Li et al. |
| 2006/0245536 | A1 | 11/2006 | Boing |
| 2007/0055142 | A1 | 3/2007 | Webler et al. |
| 2007/0073179 | A1 | 3/2007 | Afonso et al. |
| 2007/0100332 | A1 | 5/2007 | Paul et al. |
| 2007/0106146 | A1 | 5/2007 | Altmann et al. |
| 2007/0181139 | A1 | 8/2007 | Hauck |
| 2007/0244479 | A1 | 10/2007 | Beatty et al. |
| 2007/0270705 | A1 | 11/2007 | Starks |
| 2007/0299352 | A1 | 12/2007 | Harlev |
| 2008/0009758 | A1 | 1/2008 | Voth |
| 2008/0009119 | A1 | 4/2008 | Kauphusman et al. |
| 2008/0190438 | A1 | 8/2008 | Harlev |
| 2009/0163904 | A1 | 6/2009 | Miller et al. |
| 2009/0171345 | A1 | 6/2009 | Miller et al. |
| 2009/0275828 | A1 | 11/2009 | Shachar et al. |
| 2009/0306732 | A1 | 12/2009 | Rosenberg et al. |
| 2010/0168550 | A1 | 7/2010 | Byrd et al. |
| 2010/0268059 | A1 | 10/2010 | Ryu |
| 2011/0190593 | A1 | 8/2011 | McNair et al. |
| 2011/0208038 | A1 | 8/2011 | Konofagou et al. |
| 2011/0243401 | A1 | 10/2011 | Zabair et al. |
| 2012/0184863 | A1 | 7/2012 | Harlev et al. |
| 2013/0222415 | A1 | 8/2013 | Vilsmeier |
| 2013/0272592 | A1 | 10/2013 | Eichler et al. |
| 2015/0045867 | A1 | 2/2015 | Krishnan et al. |
| 2015/0133802 | A1 | 5/2015 | Nabutovsky et al. |
| 2015/0141765 | A1 | 5/2015 | Razavi et al. |
| 2015/0141858 | A1 | 5/2015 | Razavi et al. |
| 2017/0042481 | A1 | 2/2017 | Olson |

FOREIGN PATENT DOCUMENTS

| | | |
|---|---|---|
| EP | 2 757 528 A1 | 7/2014 |
| WO | 97/724981 A2 | 7/1997 |
| WO | 2012/090148 A1 | 7/2012 |

OTHER PUBLICATIONS

Bogatyrenko, Evgeniya et al., Efficient Physics-Based Tracking of Heart Surface Motion for Beating Heart Surgery Robotic Systems, International Journal of Computer Assisted Radiology and Surgery, vol. 6, No. 3, pp. 387-399, Aug. 2010.
International Search Report and Written Opinion in PCT Application No. PCT/US2015/028206 (dated Jul. 22, 2015.
Quatember, Bernhard et al., "Geometric Modeling and Motion Analysis of the Epicardial Surface of the Heart", Mathematics and Computers in Simulation, vol. 81, No. 3, pp. 608-622, Nov. 2010.
Segars, W. Paul et al., "A Realistic Spline-Based Dynamic Heart Phantom", IEEE Transactions on Nuclear Science, vol. 46, No. 3, pp. 503-506, Jun. 1999.
U.S. Appl. No. 09/107,731, filed Jun. 30, 1998 for "Chamber Mapping System".
Advisory Action dated Aug. 10, 2015; Related U.S. Appl. No. 12/347,216.
Amendment filed Jun. 25, 2015; Related U.S. Appl. No. 12/347,216.
Final Office Action dated May 4, 2015; Related U.S. Appl. No. 12/347,216.
Amendment filed Dec. 18, 2014; Related U.S. Appl. No. 12/347,216.
Non-Final Office Action dated Oct. 2, 2014; Related U.S. Appl. No. 12/347,216.
Advisory Action dated May 1, 2014; Related U.S. Appl. No. 12/347,216.
Amendment filed Apr. 24, 2014; Related U.S. Appl. No. 12/347,216.
Applicant Interview Summary, dated Apr. 21, 2014; Related U.S. Appl. No. 12/347,216.
Final Office Action dated Feb. 25, 2014; Related U.S. Appl. No. 12/347,216.
Amendment filed Feb. 4, 2014; Related U.S. Appl. No. 12/347,216.
Non-Final Office Action dated Nov. 21, 2013; Related U.S. Appl. No. 12/347,216.
Amendment filed Oct. 29, 2012; Related U.S. Appl. No. 12/347,216.
Advisory Action dated Oct. 11, 2012; Related U.S. Appl. No. 12/347,216.
Amendment filed Oct. 1, 2012; Related U.S. Appl. No. 12/347,216.
Advisory Action dated Sep. 12, 2012; Related U.S. Appl. No. 12/347,216.
Amendment filed Aug. 28, 2012; Related U.S. Appl. No. 12/347,216.
Final Office Action dated Jun. 29, 2012; Related U.S. Appl. No. 12/347,216.
Amendment filed May 14, 2012; Related U.S. Appl. No. 12/347,216.
Interview Summary, dated Feb. 28, 2012; Related U.S. Appl. No. 12/347,216.
Non-Final Office Action dated Feb. 13, 2012; Related U.S. Appl. No. 12/347,216.
Notice of Allowance dated Oct. 27, 2015; Related U.S. Appl. No. 14/328,523.
Non-Final Office Action dated Dec. 11, 2015; Related U.S. Appl. No. 14/703,460.
Non-Final Office Action dated Sep. 30, 2015; Related U.S. Appl. No. 14/270,181.
Notice of Allowance dated Dec. 8, 2015; Related U.S. Appl. No. 12/347,216.
Final Office Action dated Jan. 22, 2016; Related U.S. Appl. No. 14/270,176.
Non-Final Office Action dated Feb. 8, 2016; Related U.S. Appl. No. 14/270,181.
USPTO, "Notice of Allowance for U.S. Appl. No. 14/270,176", dated May 20, 2016.
USPTO, "Final Office Action for U.S. Appl. No. 14/703,749", dated Jan. 23, 2017.
USPTO, "Non-Final Office Action for U.S. Appl. No. 14/703,735", dated Jan. 12, 2017.
USPTO, "Non-Final Office Action for U.S. Appl. No. 14/703,744", dated Jan. 13, 2017.
University of California, San Francisco, "History AF Ablation", http://cardiology.ucsf.edu/care/clinical/electro/ablation_hist.html, accessed on Jan. 17, 2017.
Notice of Allowance dated Feb. 25, 2016; Related U.S. Appl. No. 14/328,513.
Notice of Allowance dated Feb. 25, 2016; Related U.S. Appl. No. 14/703,760.
Non-Final Office Action dated Mar. 28, 2016; Related U.S. Appl. No. 14/703,749.
Notice of Allowance dated Apr. 19, 2016; Related U.S. Appl. No. 14/270,181.

(56) References Cited

OTHER PUBLICATIONS

USPTO, "Non-Final Office Action for U.S. Appl. No. 14/270,186", dated Feb. 27, 2017.
USPTO, "Non-Final Office Action for U.S. Appl. No. 14/478,707", dated Mar. 2, 2017.
Notice of Allowance dated Apr. 18, 20017; Related U.S. Appl. No. 14/703,744.
Notice of Allowance dated Jun. 2, 20017; Related U.S. Appl. No. 14/703,744.
St. Jude Medical, "EnSite Velocity Cardiac Mapping System, Model EE3300, v.4," Feb. 28, 2013, 238 pages.
Office Action dated Jul. 5, 2017; Related U.S. Appl. No. 14/270,191.
Notice of Allowance dated May 9, 2017; Related U.S. Appl. No. 14/703,749.

\* cited by examiner

CARDIAC RESYNCHRONIZATION SYSTEM AND METHOD

RELATED APPLICATION DATA

The present application relates to and claims priority from U.S. provisional application Ser. No. 61/988,771, filed May 5, 2014, entitled "CARDIAC RESYNCHRONIZATION SYSTEM AND METHOD," which is hereby expressly incorporated by reference in its entirety.

BACKGROUND OF THE DISCLOSURE

Embodiments of the present disclosure generally relate to systems and methods of cardiac resynchronization therapy.

The St. Jude Medical MediGuide™ (MDG) cardiovascular navigation system is a three-dimensional (3-D) electromagnetic navigation system that provides real-time position and orientation of MDG sensors embedded in electrophysiological tools. The MDG system may be integrated with a fluoroscopic imaging system and tracks the sensors continuously within the imaging volume of the fluoroscopic system, on both live fluoroscopy and pre-recorded backgrounds.

SUMMARY

Systems and methods may utilize MDG motion to find sites of recent or latest mechanical activation. Additionally, embodiments may identify optimal programming settings for the system, imaging device, and/or the like. Examples of programming settings include the AV delay, the RV to LV or LV to RV delay, and in the case of multipoint pacing, the LV1 and LV2 delays.

Embodiments of the present disclosure provide systems and methods for using the MDG system to find optimal programming settings during a cardiac resynchronization therapy (CRT) implant. Certain embodiments of the present disclosure may provide other or additional systems and methods of using the MDG system for CRT optimization.

Certain embodiments of the present disclosure provide a system and method of optimizing CRT parameters using MDG sensors placed at the locations of lead implants. During the CRT implant procedure, the method may include: (1) using the distance between a MDG sensor placed in the RA lead and a MDG sensor placed in the RV lead to find the optimal AV delay; (2) mapping CS branches to find the site of latest mechanical activation while DDD pacing in the RA and RV using the chosen AV delay; (3) placing LV lead at chosen branch; and (4) using the distance between a MDG sensor placed in the RV lead and a MDG sensor placed in the middle of the chosen LV branch to find the optimal VV delay. If multi point pacing (MPP) is used, motion mapping may be repeated at the available electrode sites during BiV pacing, and LV electrodes may be identified and/or utilized to set the LV1-LV2 delay.

In at least one embodiment, operation (1) may be skipped, and optimization may occur during operation (4).

A communication protocol between the programmer and the MDG system provides smooth switching between programming parameters and MDG data collection.

Certain embodiments of the present disclosure provide a method of determining an inter-chamber delay within a heart of an individual. The method may include determining a position of a first sensor in a first chamber of the heart, determining a position of a second sensor in a second chamber of the heart, automatically computing a distance between the first and second sensors, and automatically determining the inter-chamber delay based on the automatically computing operation.

In at least one embodiment, the inter-chamber delay is an atrial-ventricular (AV) delay, the first chamber is a right ventricle of the heart, and the second chamber is a right atrium of the heart. In at least one other embodiment, the inter-chamber delay is a ventricular-ventricular (VV) delay, the first chamber is a left ventricle of the heart, and the second chamber is a right ventricle of the heart.

The method may also include automatically determining electrode settings using motion mapping at electrode sites.

The automatically determining operation may include using motion mapping at electrode sites.

The method may also include communicating programming settings between a surgical navigation sub-system and an implanted device.

The automatically computing a distance operation may include determining a sum of volumes of the first and second chambers of the heart. The distance increases as the sum increases.

The method may also include mapping coronary sinus branches, and determining a site of latest mechanical activation through the mapping operation.

The automatically computing a distance operation may include calculating a distance change index. For example, the distance change index may include subtracting an end of systole from an end of diastole, determining a difference from the subtracting operation, and dividing the difference by the end of diastole.

Certain embodiments of the present disclosure provide a system for determining an inter-chamber delay within a heart of an individual. The system may include a first sensor configured to be positioned within a first chamber of the heart, a second sensor configured to be positioned within a second chamber of the heart, wherein the first chamber differs from the second chamber, a surgical navigation sub-system configured to determine a position of the first sensor in the first chamber of the heart, and determine a position of the second sensor in the second chamber of the heart, and at least one processor configured to automatically compute a distance between the first and second sensors, and automatically determine the inter-chamber delay based on the distance between the first and second sensors.

DETAILED DESCRIPTION

Figure 1:
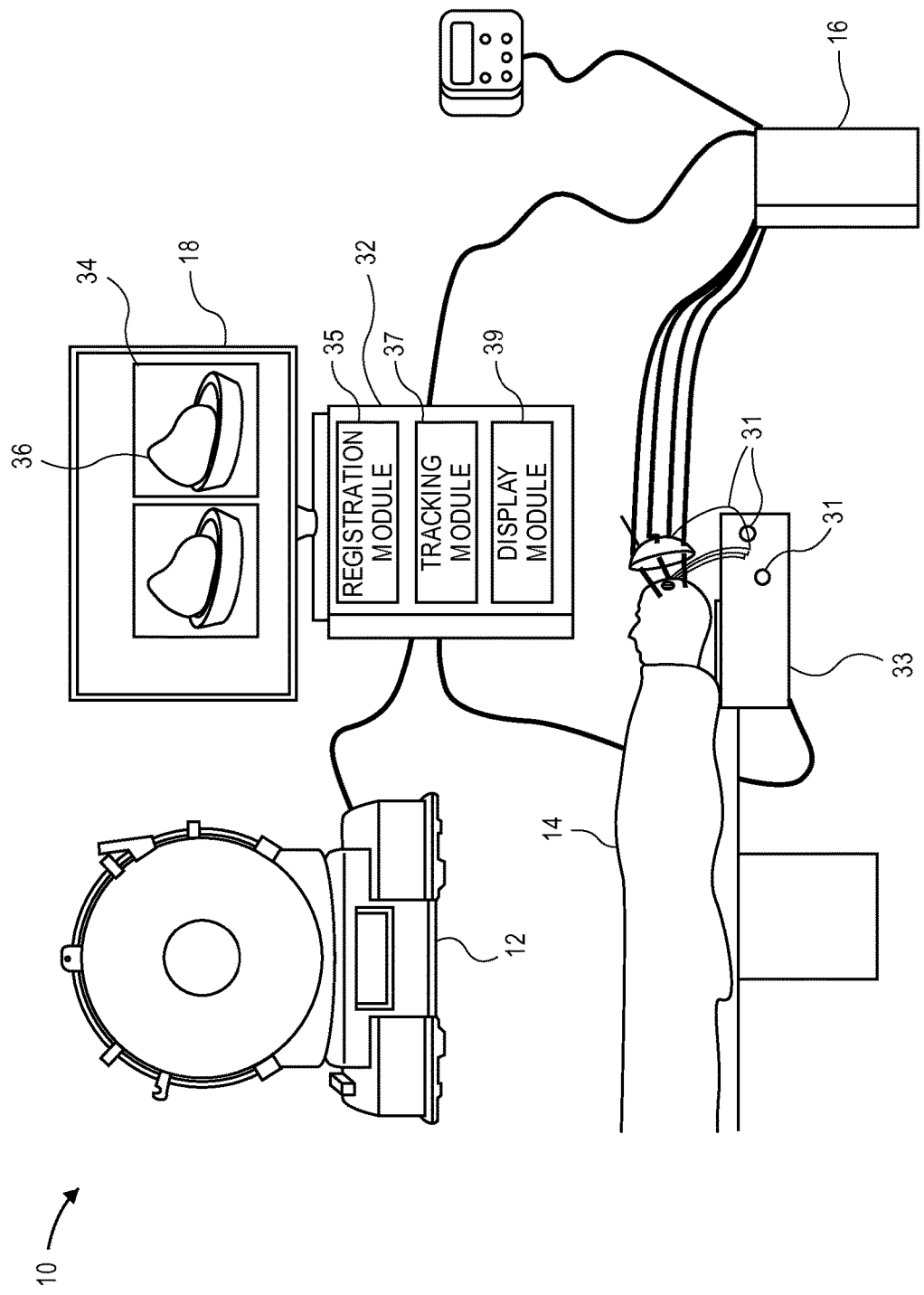
FIG. 1 illustrates a schematic diagram of a system 10, according to an embodiment of the present disclosure.

The foregoing summary, as well as the following detailed description of certain embodiments will be better understood when read in conjunction with the appended drawings. As used herein, an element or step recited in the singular and preceded by the word "a" or "an" should be understood as not necessarily excluding the plural of the elements or steps. Further, references to "one embodiment" are not intended to be interpreted as excluding the existence of additional embodiments that also incorporate the recited features. Moreover, unless explicitly stated to the contrary, embodiments "comprising" or "having" an element or a plurality of elements having a particular property may include additional elements not having that property.

The description that follows sets forth one or more illustrative embodiments. It will be apparent that the teachings herein may be embodied in a wide variety of forms, some of which may appear to be quite different from those of the disclosed embodiments. Consequently, the specific structural and functional details disclosed herein are merely representative and do not limit the scope of the disclosure. For example, based on the teachings herein one skilled in the art should appreciate that the various structural and functional details disclosed herein may be incorporated in an embodiment independently of any other structural or functional details. Thus, an apparatus may be implemented or a method practiced using any number of the structural or functional details set forth in any disclosed embodiment(s). Also, an apparatus may be implemented or a method practiced using other structural or functional details in addition to or other than the structural or functional details set forth in any disclosed embodiment(s).

Embodiments herein may be implemented with, and/or utilize aspects of, the methods and system described in the following applications:

- U.S. patent application Ser. No. 14/328,523, filed Jul. 10, 2014, titled "METHOD AND SYSTEM TO ASSESS MECHANICAL DYSSYNCHRONY BASED ON MOTION DATA COLLECTED BY A NAVIGATION SYSTEM",
- U.S. patent application Ser. No. 14/328,513, filed Jul. 10, 2014, titled "METHOD AND METHOD TO MEASURE CARDIAC MOTION USING A CARDIOVASCULAR NAVIGATION SYSTEM",
- U.S. patent application Ser. No. 14/478,707, filed Sep. 5, 2014, titled "METHOD AND SYSTEM TO IDENTIFY MOTION DATA ASSOCIATED WITH CONSISTENT ELECTRICAL AND MECHANICAL BEHAVIOR FOR A REGION OF INTEREST",
- U.S. patent application 61/988,779, filed May 5, 2014, titled "METHODS AND SYSTEMS TO CALCULATE TIME OF MECHANICAL ACTIVATION USING CHARACTERICATION MOTION DATA AREA STRAINS",
- U.S. patent application Ser. No. 14/270,181, filed May 5, 2014, titled "METHOD AND SYSTEM TO CHARACTERIZE MOTION DATA BASED ON NEIGHBORING MAP POINTS",
- U.S. patent application Ser. No. 14/270,186, filed May 5, 2014, titled "METHOD AND SYSTEM FOR CACLULATING STRAIN FROM CHARACTERIZATION DATA OF A CARDIAC CHAMBER",
- U.S. patent application Ser. No. 14/270,176, filed May 5, 2014, titled "METHOD AND SYSTEM FOR DISPLAYING A THREE DIMENSIONAL VISUALIZATION OF CARDIAC MOTION",
- U.S. patent application 61/988,735, filed May 5, 2014, titled "METHOD AND SYSTEM TO DETERMINE CARDIAC CYCLE LENGTH IN CONNECTION WITH CARDIAC MAPPING",
- U.S. patent application 61/988,763, filed May 5, 2014, titled "METHOD AND SYSTEM TO EQUALIZING CARDIAC CYCLE LENGTH BETWEEN MAP POINTS",
- U.S. patent application 61/988,767, filed May 5, 2014, titled "METHOD AND SYSTEM TO SUBDIVIDE A MAPPING AREA FOR MECHANICAL ACTIVATION ANALYSIS", and
- U.S. patent application 61/988,774, filed May 5, 2014, titled "SYSTEM AND METHOD FOR EVALUATING LEAD STABILITY OF AN IMPLANTABLE MEDICAL DEVICE".

All of the above cited applications are expressly incorporated herein by reference in their entireties.

FIG. 1 illustrates a schematic diagram of a system 10, according to an embodiment of the present disclosure. The system 10 may include an imaging sub-system 12 configured to acquire images of a patient 14, a positioning sub-system 16, and a surgical navigation sub-system 18. The imaging sub-system 12 is used to acquire one or more images of the patient 14. For example, the imaging sub-system 12 is configured to acquire one or more images of a heart of a patient. The positioning sub-system 16 may be used to position probes into the patient 14. The surgical navigation sub-system 18 may be used in conjunction with the acquired images to allow a surgeon to visualize placement of the probes of the positioning sub-system 16 into the patient 14. Alternatively, the system 10 may not include the positioning sub-system 16. Further, the system may be used with respect to imaging and navigation with respect to other anatomical structure of the patient other than the heart.

The imaging sub-system 12 may include one or more of an X-ray, fluoroscope, CT, MRI, Positron Emission Tomography (PET), ultrasound, or other such imaging systems. For example, the imaging sub-system 12 may include MRI and CT imaging systems. In general, the imaging sub-system 12 may include a radiation source or generator and a radiation sensor or detector.

The surgical navigation sub-system 18 may include a main housing 32, such as a computer workstation, operatively connected to a display 34 that is configured to display images 36 thereon. The display 34 may be or include a monitor, screen, television, or the like, for example. The surgical navigation sub-system 18 may be used to electromagnetically track movement of probes of the positioning sub-system 16 before and during a procedure. The surgical navigation sub-system 18 may be used to automate surgical planning and lead or probe placement, while displaying a current position of the lead or probe within the patient anatomy.

The main housing 32 may contain a registration module 35, a tracking module 37, and a display module 39. The registration module 35 may be configured to register reference members, such as fiducials, coils, and/or the like, of a frame, probe, or the like, with one or more reference markers, points, or the like of images of patient anatomy. The tracking module 37 is configured to track movement of a probe, for example, with respect to an area or volume, such as within the heart. The display module 39 is configured to display a representation of the probe, for example, on one or more acquired images on the display, based on the movement of the probe as determined by the tracking module 37.

Each of the modules 35, 37, and 39 may include any processor-based or microprocessor-based system including systems using microcontrollers, reduced instruction set computers (RISC), application specific integrated circuits (ASICs), logic circuits, and any other circuit or processor capable of executing the functions described herein. For example, each of the modules 35, 37, and 39 may be or include at least one processor and at least one memory. The above are exemplary only, and are thus not intended to limit in any way the definition and/or meaning of the term "computer" or "module."

The surgical navigation sub-system 18 may also include a tracking assembly 33 in the vicinity of the patient 14. For example, the tracking assembly 33 may include a housing situated on or underneath a platform on which the patient 14 rests. The tracking assembly 33 may include one or more transmitters 31 configured to radiate a field, such as an electromagnetic field, within the vicinity of the patient 14. The field radiated by the transmitters 31 may be detected by a position detector of a probe, for example, as described below.

The surgical navigation sub-system 18 may be used with various anatomical structures. For example, the surgical navigation sub-system 18 may be used to track movement of devices, instruments, probes, and the like within the heart of the patient.

The surgical navigation sub-system may be further described with respect to U.S. Pat. No. 7,811,294, entitled "Automatic Guidewire Maneuvering System and Method," which is hereby incorporated by reference in its entirety. The surgical navigation sub-system may be used to visualize movement of the probe with respect to one or more images of the heart. The surgical navigation sub-system may be used to automatically move a probe according to a surgical plan. Optionally, the surgical navigation sub-system may be used to simply superimpose an image of the probe with respect to the image(s) of the heart, brain, or the like in order to track movement of the surgical probe with respect thereto.

Figure 2:
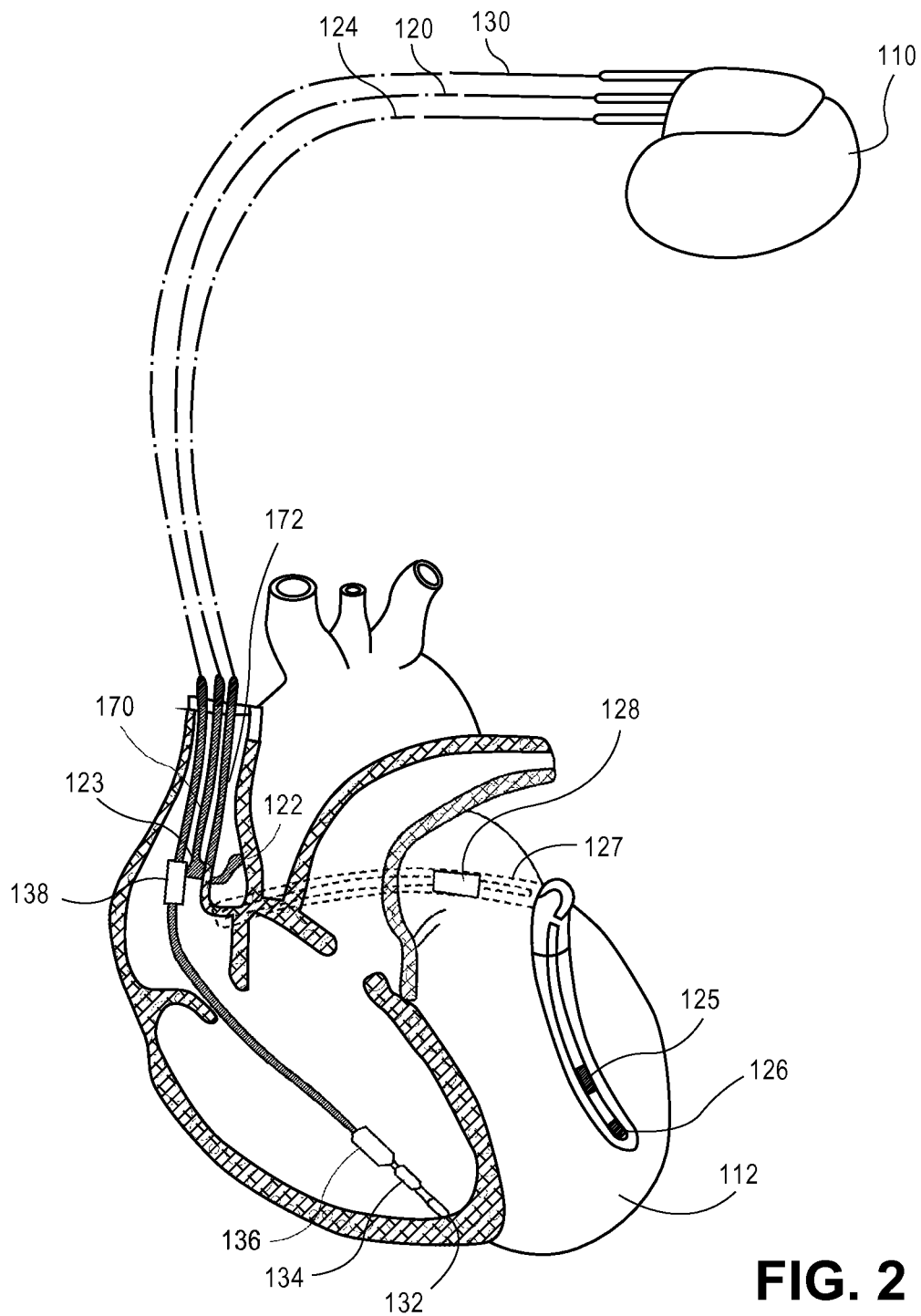
FIG. 2 illustrates a simplified view of an exemplary implantable medical device (IMD) in electrical communication with at least three leads implanted into a patient's heart, according to an embodiment of the present disclosure.

FIG. 2 illustrates an IMD 110 in electrical communication with a patient's heart 112 by way of three leads 120, 124 and 130 suitable for delivering multi-chamber stimulation and/or shock therapy. To sense atrial cardiac signals and to provide right atrial chamber stimulation therapy, the IMD 110 is coupled to an implantable right atrial (RA) lead 120 including at least one atrial tip electrode 122 that typically is implanted in the patient's right atrial appendage. The right atrial lead 120 may also include an atrial ring electrode 123 to allow bipolar stimulation or sensing in combination with the atrial tip electrode 122.

To sense the left atrial and left ventricular cardiac signals and to provide left-chamber stimulation therapy, the IMD 110 is coupled to a lead 124 designed for placement in the "coronary sinus region" via the coronary sinus ostium in order to place a distal electrode adjacent to the left ventricle and additional electrode(s) adjacent to the left atrium. As used herein, the phrase "coronary sinus region" refers to the venous vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

Accordingly, the lead 124 is designed to: receive atrial and/or ventricular cardiac signals; deliver left ventricular pacing therapy using at least one left ventricular tip electrode 126 for unipolar configurations or in combination with left ventricular ring electrode 125 for bipolar configurations; and/or deliver left atrial pacing therapy using at least one left atrial ring electrode 127 as well as shocking therapy using at least one left atrial coil electrode 128.

The IMD 110 is also shown in electrical communication with the patient's heart 112 by way of an implantable right ventricular (RV) lead 130 including, in the embodiment, a right ventricular (RV) tip electrode 132, a right ventricular ring electrode 134, a right ventricular coil electrode 136, a superior vena cava (SVC) coil electrode 138, and so on.

Typically, the right ventricular lead 130 is inserted transvenously into the heart 112 so as to place the right ventricular tip electrode 132 in the right ventricular apex such that the RV coil electrode 136 is positioned in the right ventricle and the SVC coil electrode 138 will be positioned in the right atrium and/or superior vena cava. Accordingly, the right ventricular lead 130 is capable of receiving cardiac signals, and delivering stimulation in the form of pacing and shock therapy to the right ventricle.

The IMD may be one of various types of implantable devices, such as, for example, an implantable pacemaker, implantable cardioverter-defibrillator ("ICD"), neurostimulator, electrophysiology ("EP") mapping and radio frequency ("RF") ablation system, or the like. Optionally, the IMD may be configured to provide leadless therapy.

Figure 3:
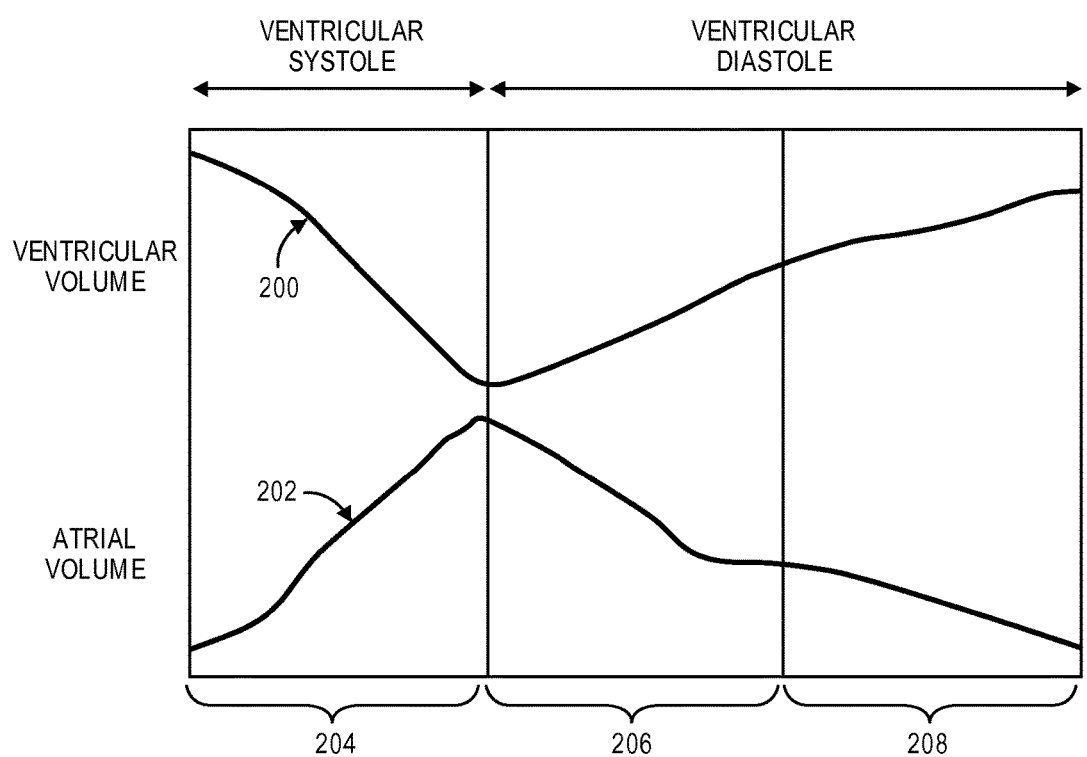
FIG. 3 illustrates representative ventricular and atrial volume curves, according to an embodiment of the present disclosure.

FIG. 3 illustrates representative ventricular and atrial volume curves 200 and 202, respectively, according to an embodiment of the present disclosure. Referring to FIGS. 1-3, embodiments of the present disclosure may use the distance between a MDG sensor 170 placed in the RA lead and a MDG sensor 172 placed in the RV lead to find a select atrial-ventricular (AV) delay. The concept behind the desired AV delay selection is that at a select (e.g. optimal) AV delay, the atrium makes a maximal contribution to ventricular filling. In order for that to occur, the atrium completes its emptying immediately before the ventricle begins contracting and the ventricle begins contracting as the atrium is emptied. The ventricle then contracts while the atrium is filling. Atrial and ventricular volume curves during a cardiac cycle are shown in FIG. 3. As shown in FIG. 3, the cardiac cycle is divided into thirds—during the first third 204 of the cardiac cycle, which starts shortly after the R-peak of the surface ECG, the atrium is filling and the ventricle is in systole and is emptying. In the next third 206 of the cardiac cycle, the atrium is full and the ventricle is in early diastole. In the final third 208 of the cardiac cycle, the atrium is emptying and the ventricle continues into late diastole.

The distance between the MDG sensor in the atrium and the MDG sensor in the ventricle may be related to the sum of the volumes of the two chambers. The distance increases as the sum of the volumes increases. Because the two volumes may be out of phase with each other, the sum may be relatively flat. Therefore, the optimal AV delay may result in a relatively flat distance between the two sensors during the duration of the cardiac cycle. Flatness of the curve may be quantified in different ways—by preventing, minimizing, or otherwise reducing peaks beyond some threshold, by finding the slope of the curve and keeping it below some threshold, or using any other known method.

Coronary sinus (CS) branches may be mapped to find the site of latest mechanical activation while DDD pacing in the RA and RV uses the chosen AV delay. An LV lead may be placed at the chosen CS branch. MDG data may be collected at different locations in the CS branches to find site(s) of latest mechanical activation and place the LV lead there. Candidate branches may be mapped while pacing the heart. The DDD mode of pacing may be used, with the AV delay set to the optimal AV delay. However, this could also be done while VVI or DDI pacing.

Next, the system and method may use the distance between a MDG sensor placed in the RV lead and a MDG sensor placed in the LV lead to find the optimal VV delay. An MDG-enabled tool (for example, a guidewire or stylet) may be placed inside the lead already implanted in the vein chosen in the previous step. Another MDG-enabled tool may be placed inside the RV lead. In addition, surface ECG may be collected.

The system then paces the heart using the AV delay determined above, which may include various pre-defined VV delays, pausing at each setting to take measurements from the MDG sensors. Each measurement contains at least one cardiac cycle. The x,y,z data may then be preprocessed. The distance between the sensor at the LV location and the sensor at the RV location may be found for each VV delay during the cardiac cycle. End of systole time is determined as the time within a window after the R-peak on the ECG when the distance between the two sensors may be smallest. End of diastole time is determined as the time at the R-peak or at a pre-defined percentage of the cardiac cycle length from an identifiable feature of the surface ECG. For each VV delay, the distance between the LV and RV locations may be found at the end of systole (ESD) and at the end of diastole (EDD). A parameter, such as the distance change index (DCI), may be calculated:

$$DCI = \frac{EDD - ESD}{EDD}$$

The VV delay with the greatest DCI may be chosen as the optimal delay. If AV optimization was not performed, rather than just testing VV delays, the system may cycle through various permutations of AV and VV delays.

The computations and analyses described in the present application may be performed by one or more processors, which may include or be communicatively coupled to one or more memories.

Alternatively, a system and method to optimize the AV/VV delays may be related to a method used in TDI echocardiography optimization in which wall velocity is converted to acceleration and cross-correlation of opposing wall accelerations is found. Settings that yield high correlation may be used. In motion mapping, a similar analysis may be performed. A cross correlation of the second time derivatives of motion at the LV and the RV may be found. High correlation indicates higher level of synchrony. Therefore, CRT settings that yield a select level (e.g. the highest) correlation may be used.

In at least one embodiment, both the DCI analysis and the cross-correlation analysis may be performed. If the DCI analysis shows equivalent performance for several VV delays, the cross-correlation analysis may be used to choose between the candidates.

If MPP is desired, repeat motion mapping at the available electrode sites while BiV pacing and identify which LV electrodes to utilize and how to set the LV1-LV2 delay.

At least one cardiac cycle of MDG motion data may be collected at each LV electrode location while BiV pacing using the VV delay determined above. For example, an MDG-enabled guidewire may be placed inside the LV lead with the MDG sensor aligned with each electrode. If any of the electrodes are located in a scar region (as determined by low peak to peak voltage, MRI, or another method), they may not be considered as candidates for stimulation.

The time of the onset of mechanical activation may be found at each collection site, either with displacement or strain. The electromechanical delay may be computed as the time from the LV stimulation pulse to the time of the onset of mechanical activation. The electromechanical delays (EMD) are compared at the electrode sites. The two sites with the longest EMD may be used as the two LV electrodes. The site with the absolute longest EMD may be set as LV1 and the site with the second longest EMD may be set as LV2, with the difference between their EMD values as the LV1-LV2 delay. If the two longest EMD values are the same, the LV-LV delay may be set to the minimum available value.

In at least one embodiment, the user interface for programming and mapping may be contained on the MDG system. The user interface may guide the user through the optimization steps described above. The user interface may indicate the general location where each MDG tool is to be placed based on where the user is in the procedure (e.g., "Place MDG tool in RA and place MDG tool in RV") and provides the options for delay settings. The user initiates each set of tests. The MDG system may communicate with the device programmer via a cable or through a wireless connection, which may in turn reprogram the patient's device for each setting, and initiate pacing. The MDG system then makes the appropriate motion measurements and performs the methods described above to suggest a parameter set that synchronizes cardiac motion.

Various embodiments described herein provide a tangible and non-transitory (for example, not an electric signal) machine-readable medium or media having instructions recorded thereon for one or more processors or computers to operate a system to perform one or more embodiments of methods described herein. The medium or media may be any type of CD-ROM, DVD, floppy disk, hard disk, optical disk, flash RAM drive, or other type of computer-readable medium or a combination thereof.

The various embodiments and/or components, for example, the sub-systems, systems, control units, modules, or components and controllers therein, also may be implemented as part of one or more computers or processors. The computer or processor may include a computing device, an input device, a display unit and an interface, for example, for accessing the Internet. The computer or processor may include a microprocessor. The microprocessor may be connected to a communication bus. The computer or processor may also include a memory. The memory may include Random Access Memory (RAM) and Read Only Memory (ROM). The computer or processor may also include a storage device, which may be a hard disk drive or a removable storage drive such as a floppy disk drive, optical disk drive, and the like. The storage device may also be other similar means for loading computer programs or other instructions into the computer or processor.

As used herein, the term "computer" or "module" may include any processor-based or microprocessor-based system including systems using microcontrollers, reduced instruction set computers (RISC), application specific integrated circuits (ASICs), logic circuits, and any other circuit or processor capable of executing the functions described herein. The above examples are exemplary only, and are thus not intended to limit in any way the definition and/or meaning of the term "computer" or "module."

The computer or processor executes a set of instructions that are stored in one or more storage elements, in order to process input data. The storage elements may also store data or other information as desired or needed. The storage element may be in the form of an information source or a physical memory element within a processing machine.

The set of instructions may include various commands that instruct the computer or processor as a processing machine to perform specific operations such as the methods and processes of the various embodiments of the subject matter described herein. The set of instructions may be in the form of a software program. The software may be in various forms such as system software or application software. Further, the software may be in the form of a collection of separate programs or modules, a program module within a larger program or a portion of a program module. The software also may include modular programming in the form of object-oriented programming. The processing of input data by the processing machine may be in response to user commands, or in response to results of previous processing, or in response to a request made by another processing machine.

As used herein, the terms "software" and "firmware" may be interchangeable, and include any computer program stored in memory for execution by a computer, including RAM memory, ROM memory, EEPROM memory, and non-volatile RAM (NVRAM) memory. The above memory types are exemplary only, and are thus not limiting as to the types of memory usable for storage of a computer program.

While various spatial and directional terms, such as top, bottom, lower, mid, lateral, horizontal, vertical, front, and the like may be used to describe embodiments, it is understood that such terms are merely used with respect to the orientations shown in the drawings. The orientations may be inverted, rotated, or otherwise changed, such that an upper portion is a lower portion, and vice versa, horizontal becomes vertical, and the like.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the disclosure without departing from its scope. While the dimensions, types of materials and coatings described herein are intended to define the parameters of the disclosure, they are by no means limiting and are exemplary embodiments. Many other embodiments will be apparent to those of skill in the art upon reviewing the above description. The scope of the disclosure should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means—plus-function format and are not intended to be interpreted based on 35 U.S.C. §112(f), unless and until such claim limitations expressly use the phrase "means for" followed by a statement of function void of further structure.

What is claimed is:

1. A method of determining an inter-chamber delay within a heart of an individual, the method comprising:
    under control of one or more processors configured to execute program instruction;
    determining a position of a first sensor in a first chamber of the heart;
    determining a position of a second sensor in a second chamber of the heart;
    repeating the determining operations for multiple inter-chamber delays;
    automatically computing distance changes between the first and second sensors in connection with the corresponding inter-chamber delays; and
    automatically determining a select inter-chamber delay from the inter-chamber delays based on the distance changes computed in the automatically computing operation.

2. The method of claim 1, wherein the inter-chamber delay is an atrial-ventricular (AV) delay, wherein the first chamber is a right ventricle of the heart, and wherein the second chamber is a right atrium of the heart.

3. The method of claim 1, wherein the inter-chamber delay is a ventricular-ventricular (VV) delay, wherein the first chamber is a left ventricle of the heart, and wherein the second chamber is a right ventricle of the heart.

4. The method of claim 1, wherein the distance change, associated with at least one of the inter-chamber delays, represents a distance change index calculated based on changes in location of the first sensor for first and second points in a cardiac cycle and based on changes in location of the second sensor for the first and second points in the cardiac cycle.

5. The method of claim 4, wherein the first and second points in the cardiac cycle correspond to end of systole (ESD) and end of diastole (EDD), respectively, and wherein the distance change index (DCI) is based on DCI=(EDD−ESD)/EDD.

6. The method of claim 1, further comprising communicating programming settings between a surgical navigation sub-system and an implanted device.

7. The method of claim 1, wherein the automatically computing a distance operation comprises determining a sum of volumes of the first and second chambers of the heart, wherein the distance increases as the sum increases.

8. The method of claim 1, further comprising:
    mapping coronary sinus branches; and
    determining a site of latest mechanical activation through the mapping operation.

9. The method of claim 1, wherein the automatically computing a distance operation comprises calculating a distance change index.

10. The method of claim 9, wherein the calculating a distance change index comprises:
    subtracting an end of systole from an end of diastole;
    determining a difference from the subtracting operation; and
    dividing the difference by the end of diastole.

11. A system for determining an inter-chamber delay within a heart of an individual, the system comprising:
    a first sensor configured to be positioned within a first chamber of the heart;
    a second sensor configured to be positioned within a second chamber of the heart, wherein the first chamber differs from the second chamber;
    a surgical navigation sub-system configured to:
        determine a position of the first sensor in the first chamber of the heart,
        determine a position of the second sensor in the second chamber of the heart, and
        repeat the determining operations for multiple inter-chamber delays; and
    at least one processor configured to automatically compute distance changes between the first and second sensors in connection with the corresponding inter-chamber delays, and automatically determine a select inter-chamber delay from the inter-chamber delays based on the distance changes between the first and second sensors.

12. The system of claim 11, wherein the inter-chamber delay is an atrial-ventricular (AV) delay, wherein the first chamber is a right ventricle of the heart, and wherein the second chamber is a right atrium of the heart.

13. The system of claim 11, wherein the inter-chamber delay is a ventricular-ventricular (VV) delay, wherein the first chamber is a left ventricle of the heart, and wherein the second chamber is a right ventricle of the heart.

14. The system of claim 11, wherein the at least one processor is further configured to automatically determine electrode settings using motion mapping at electrode sites.

15. The system of claim 11, wherein the at least one processor is configured to use motion mapping at electrode sites to automatically determine the inter-chamber delay.

16. The system of claim 11, wherein the surgical navigation sub-system and an implanted device are configured to communicate programming settings.

17. The system of claim 11, wherein the at least one processor is configured to automatically compute the distance by determining a sum of volumes of the first and second chambers of the heart, wherein the distance increases as the sum increases.

18. The system of claim 11, wherein one or both of the surgical navigation sub-system or the at least one processor is configured to map coronary sinus branches, and determine a site of latest mechanical activation through the map.

19. The system of claim 11, wherein the at least one processor is configured to automatically compute a distance operation by calculating a distance change index.

20. The system of claim 19 wherein the at least one process is configured to calculate the distance change index by subtracting an end of systole from an end of diastole, determine a difference from the subtracting operation, and divide the difference by the end of diastole.

* * * * *